US006416294B1

United States Patent
Zengerle et al.

(10) Patent No.: US 6,416,294 B1
(45) Date of Patent: Jul. 9, 2002

(54) MICRODOSING DEVICE

(75) Inventors: Roland Zengerle; Michael Freygang, both of Villingen-Schwenningen; Nicolaus Hey, Eschbronn; Holger Gruhler, Tuningen, all of (DE)

(73) Assignee: Hans-Schickard-Gesellschaft fur angewandte Forschung e.V., Villingen-Schwenningen (DE)

( * ) Notice: Subject to any disclaimer, the term of this patent is extended or adjusted under 35 U.S.C. 154(b) by 0 days.

(21) Appl. No.: 09/582,917

(22) PCT Filed: Jan. 14, 1999

(86) PCT No.: PCT/EP99/00185

§ 371 (c)(1), (2), (4) Date: Aug. 7, 2000

(87) PCT Pub. No.: WO99/37400

PCT Pub. Date: Jul. 29, 1999

(30) Foreign Application Priority Data

Jan. 22, 1998 (DE) .......................................... 198 02 368

(51) Int. Cl.[7] .............................................. F09B 17/00
(52) U.S. Cl. ...................................... 417/53; 417/413.3
(58) Field of Search ................................ 417/53, 413.2, 417/413.3

(56) References Cited

U.S. PATENT DOCUMENTS

| 3,963,380 A | * | 6/1976 | Thomas, Jr. et al. ......... 417/322 |
| 4,216,477 A | * | 8/1980 | Matsuda et al. ......... 346/140 R |
| 4,231,287 A | * | 11/1980 | Smiley ........................ 417/322 |
| 4,543,044 A | * | 9/1985 | Simmons ..................... 417/342 |
| 4,983,876 A | * | 1/1991 | Nakamura et al. ........... 310/328 |
| 5,401,140 A | * | 3/1995 | Anderson .................... 417/63 |
| 5,759,014 A | * | 6/1998 | Van Lintel ............... 417/413.3 |

FOREIGN PATENT DOCUMENTS

| DE | 197 06 513 A | 8/1998 |
| EP | 0 439 327 A | 7/1991 |
| EP | 0703364 A | 3/1996 |
| EP | 0 725 267 A | 8/1996 |
| WO | WO 97 10435 A | 3/1997 |

OTHER PUBLICATIONS

A. Jahns, "Pipettieren und Dispensieren", Sonderuck aus mta–Fachzeitschrift der Technischen Assistenten in der Medizin, Jahrgang 8 (1993), Heft 12, pp 1166–1172, Umschau Zeitschrift–Tenverlag.

(List continued on next page.)

*Primary Examiner*—Charles G. Freay
(74) *Attorney, Agent, or Firm*—Dougherty & Clements LLP (57) ABSTRACT

A volume sensor-free microdosing device comprises a pressure chamber which is at least partly delimited by a displacer, an actuating device for actuating the displacer, the volume of the pressure chamber being adapted to the changed by actuating the displacer, a media reservoir which is in fluid communication with the pressure chamber, an outlet opening which is in fluid communication with the pressure chamber, and a control mechanism. The control mechanism drives the microdosing device in such a way that a small change of volume of the pressure chamber volume is effected per unit time by a movement of the displacer from a first position to a predetermined second position, the second position of the displacer defining a larger volume of the pressure chamber than the first position, so as to suck a fluid volume into the pressure chamber, and that, in a second phase, a large volume change of the pressure chamber volume is effected per unit time by a movement of the displacer from the second position to the first position, so as to eject a defined fluid volume from the outlet opening in this way.

24 Claims, 6 Drawing Sheets

OTHER PUBLICATIONS

N. Schwesinger, "Planarer Tintenstrahldruckkopf", F&M, 11–12, pp 456–460; 1993.

H. Bentin, M. Doering, W. Radtke, U. Rothgordt, "Physical Properties of Micro–Planar Ink–Drop Generators", J. Imagin Technology 3, pp 152–155; 1986.

Wolfgang Wehl, "Tintendrucktechnologie: Paradigma und Motor der Mikrosystemtechnik, Feinwerktechnik & Messtechnik", Part I in issue 6/95, Part 2 in issue 9/95.

"Mikrodosierung", company journal of microdrop GmbH, Norderstedt; 1995.

* cited by examiner

MICRODOSING DEVICE

PRIORITY

Applicants claim the benefit of priority from International Application PCT/EP99/00185.

BACKGROUND OF THE INVENTION

1. Field of the Invention

The present invention relates to a microdosing device.

2. Description of Prior Art

Precise dosing of extremely small volumes of fluid in the range between 0.01 µl and 1 µl is of great and decisive importance e.g. in the fields of biotechnology, DNA analytical chemistry and combinatorial chemistry. According to the prior art, dispensers or pipettes are predominantly used for dosing small volumes. In these cases, the volume to be dosed is displaced either directly, by a so-called piston-type direct displacement, or via an intermediate air cushion. In this respect, reference is made e.g. to the article "Pipettieren und Dispensieren", A. Jahns, Fachzeit-schrift der Technischen Assistenten in der Medizin, volume 8 (1993), No. 12, pages 116–1172, Umschau Zeitschriftenver-lag.

Air-cushion pipettes are suitable for dosing volumes between 0.01 µl and 5 ml, accuracies of ±2–3% being achieved in the case of volumes exceeding 1 µl. In the case of smaller volumes, however, the accuracies achieved are only accuracies of approx. ±10% due to surface effects at the tip of the pipette. The limited dosing accuracy in the case of smaller volumes is predominantly due to the fact that the tip of the pipette or dispenser must be immersed into the medium to be dosed, whereby the dosing amount will be influenced by effects such as surface tension, wetting and hydrostatic pressure. In order to avoid these problems as well as the risk of carrying over media due to immersion, a dosing system should be based on the discharge of the dosed volume in a free jet. Direct-displacement dispensing devices offer this additional advantage, but only in the case of volumes of approx. 10 µl and more.

Known systems discharging extremely small volumes of fluid in a free jet are ink-jet printheads. Ink-jet printheads are known which are based on two fundamentally different principles, viz. those which are effective making use of thermal transducers and those which are effective making use of piezoelectric transducers. In this respect, reference is made to the publications N. Schwesinger: "Planarer Tintenstrahldruckkopf". F&M, 11–12; pages 456–460; 1993; H. Bentin, M. Doering, W. Radtke, U. Rothgordt: "Physical Properties of Micro-Planar Ink-Drop Generators". J. Imaging Technology, 3; pages 152–155; 1986; and Wolfgang Wehl; Tinten-drucktechnologie; Paradigma und Motor der Mikrosystemtechnik; Feinwerktechnik & MeBtechnik; part 1 in edition 6/95, part 2 in edition 9/95.

In the case of printheads operating according to the "drop-on-demand" principle, a small ink drop is flung in a free jet onto a paper after the application of a voltage pulse. A typical drop diameter is approx. 60 µm, i.e. the volume is approx. 0.0001 µl. Normally, these printheads are, however, only adapted to be used in combination with special inks. Media which are used e.g. in the field of biotechnology are in most cases very different from these inks as far as viscosity and surface tension are concerned. However, the viscosity and the surface tension substantially influence the size of the drops and, consequently, the volume dosed. Furthermore, a generation of drops is only possible in a very limited viscosity range. The volume of the individual drops can, moreover, only be modified in a very limited range by modifying the control pulses.

Furthermore, dosing systems are known, which are also capable of generating drops in the case of media having strongly different viscosities. Such a system is described e.g. in the publication "Mikrodosierung", company publication of the firm of microdrop GmbH, Norderstedt, 1995. As in the case of ink-jet printheads, the drop volume is here determined predominantly by the size of the nozzle diameter. only to a very limited extent can it also be influenced by the electric control of the actuator. As in the case of ink-jet printheads, the process of drop tearing at the nozzle depends, however, on the physical properties of the media to be dosed, i.e. on the viscosity, the surface tension, etc. The exact size of the drops is therefore again strongly media-dependent. The dosing of a desired volume, which lies in the range between 0.1 µp and 1 µl in most cases, is based the counting of individual drops of the same size. The typical volume of an individual drop is smaller than 0.001 µl. Since the volume errors of the individual drops will, however, accumulate in this process, the dosing accuracy is strongly limited.

An increase of this dosing accuracy is only possible with the aid of complicated and expensive systems. An image processing system can, for example, be used by means of which the size of the individual drops can be determined and the number of drops required can be calculated during a dosing process. Furthermore, according to an alternative method of increasing the dosing accuracy, a fluorescent substance can be admixed to the medium to be dosed. In the case of this alternative method, the dosing process will be finished when the intensity of the fluorescent signal reaches the set value. It is, however, easily evident that the above-mentioned methods of increasing the dosing accuracy are both very complicated and expensive.

EP-A-0439327 discloses a control system for a micropump, which is adapted to be used e.g. in a dosing device. The control system selectively controls the generation of drive pulses so as to control the discharge of fluid through the pump. This known control for a micropump uses respective square-wave signals having different amplitudes so as to control a piezoelectric driver element which serves to drive a pump membrane.

EP-A-0725267 discloses an electrically controllable micropipette for handling extremely small fluid volumes in the range of a few hundred pl to a few µl. The main component of this known micropipette is a micromembrane pump operated as a microejection pump; a second micromembrane pump can additionally be provided, which is implemented as a micropressure or a microsuction pump. Each of these respective pumps is controlled by square-wave voltages.

In the prior, non-prepublished German application 19706513.9-52 owned by the applicant of the present application and filed on Feb. 19, 1997, a microdosing device is disclosed, which permits a discharge of exactly defined volumes of fluid. This application discloses a microdosing device comprising a pressure chamber which is at least partly delimited by a displacer. An actuating device for actuating the displacer is provided, the volume of the pressure chamber being adapted to be changed by actuating the displacer. A media reservoir is in fluid comunication with the pressure chamber via a first fluid line, whereas an outlet opening is in fluid communication with the pressure chamber via a second fluid line. For causing a defined fluid volume to be discharged from the outlet opening, the above-mentioned publication discloses that there are provided a means for detecting the respective position of the displacer and a control means which is connected to the actuating device and to the means for detecting the position of the displacer, the control means controlling the actuating device on the basis of the detected position of the displacer or on the basis of displacer positions detected during at least one preceding dosing cycle.

By means of the microdosing device disclosed in the above-mentioned German application 19706513.9-52 it is possible to eject exactly defined volumes of fluid independently of the vicosity of the fluid to be dosed by controlling the actuator of the displacer on the basis of the output signals of the volume sensor. It follows that the defined fluid volume is almost independent of the viscosity, surface tensions, etc. of the medium to be dosed. It follows that media which differ with regard to viscosity and surface tensions can be dosed according to the above-mentioned German application, such media being used e.g. in the field of biotechnology.

SUMMARY OF THE INVENTION

It is the object of the present invention to provide an uncomplicated microdosing device permitting, within an operating range, a dosing operation which is independent of the viscosity of a medium to be dosed.

This object is achieved by a volume sensor-free microdosing device comprising a pressure chamber which is at least partly delimited by a displacer, an actuating device for actuating the displacer, the volume of the pressure chamber being adapted to be changed by actuating the displacer, a media reservoir which is in fluid communication with the pressure chamber, an outlet opening which is in fluid communication with the pressure chamber, and a control means. With the aid of the control means the microdosing device is driven in such a way that a small change of volume is effected per unit time by a movement of the displacer from a first position to a predetermined second position, the second position of the displacer defining a larger volume of the pressure chamber than the first position, so as to suck a fluid volume into the pressure chamber. During a second phase, the control means drives the microdosing device in such a way that, by means of a movement of the displacer from the second position to the first position, a large volume change of the pressure chamber volume is effected per unit time so as to eject a defined fluid volume from the outlet opening in this way.

The present invention is based on the finding that it is possible to provide a viscosity-independent dosage in a sufficiently large, interesting operating range even if the volume sensor means, i.e. a means for detecting the position of the displacer, is dispensed with in the microdosing device disclosed in the above-mentioned German application 19706513.9-52. This viscosity independence of the dosing process, which suffices for many cases of use and which is described in the present application, is not disclosed in the above-mentioned German application 19706513.9-52, since the ejection of a defined fluid volume, essentially viscosity independent, is there precisely carried out on the basis of such a volume sensor means.

According to the present invention, fluid is ejected due to a direct displacement of the fluid, in contrast to acoustic principles which are used in most ink printheads. In such ink printheads, especially in printheads which are driven piezoelectrically, a pressure wave is normally produced in the dosing chamber which propagates in the direction of the nozzle and which causes the drop to tear at the nozzle. The drop diameter will here essentially correspond to twice the cross-section of the nozzle. In contrast to this, a pressure wave is generated by a vapour bubble in known, so-called bubble jet printers; the displacement caused by the vapour bubble is limited to a volume of approx. 50 to 100 pl due to the size of the vapour bubble and cannot be substantially increased due to physical principles. This will typically have the effect that an individual drop having a size of the order of twice the cross-section of the nozzle will tear, whereas according to the present invention a jet of fluid is obtained whose total volume is much larger than this individual drop.

In each mechanism used for generating individual drops, the exact tearing of the drop and, consequently, the dosed fluid volume depends on many details, such as e.g. the viscosity, the surface tension of the fluid, the temperature, the control voltage, etc. In these individual-drop mechanisms both the drop size and the formation of a "drop tail", which is produced when the drop tears, differ. It follows that a different viscosity leads to a variation of the dosed volume of an individual drop, the absolute dosing errors of each individual drop being summed up by the summation of the individual drops when the whole volume to be dosed is being produced. Hence, the relative dosing error of the total volume corresponds to the relative dosing error of each individual drop.

It is now the concept of the present invention to eject a substantially larger amount of fluid than an individual drop with high kinetic energy. The ejected amount of fluid may have the volume of approx. 10 to 1,000 individual drops, these values being, however, only indicated by way of example. According to the present invention, the effects occurring when the fluid jet tears will therefore only influence the beginning and the end of the fluid jet, and, with respect to the total dosing volume, these effects will only be of secondary importance. The predominant portion of the fluid amount discharged from the outlet opening or the nozzle is determined by inertia and friction.

It follows that in the case of the method according to the present invention, which is based on a direct displacement of the fluid, the error caused by the tearing of a drop will occur only once for the whole amount of fluid. Whereas the summation of 10 to 1,000 individual drops in individual-drop meachanisms entails a summation of the erros the individual drops, the present invention permits, roughly speaking, the error to be reduced by the number of individual drops contained in the dosed fluid amount. In this connection, reference should be made to the fact that also according to the present invention the fluid jet can disintegrate into individual drops when it has left the nozzle. This will, however, no longer have any influence on the total dosing amount, since the fluid has already left the nozzle. Moreover, an even more precise dosage can be achieved when the actuating device and the displacer are implemented with a stiffness of such a nature that the displacer is essentially forcibly controlled.

The media reservoir can be connected to the pressure chamber via a first fluid line, whereas the outlet opening can be connected to the pressure chamber via a second fluid line.

According to a preferred embodiment of the present invention, the control means controls the actuating device in such a way that the volume changes described are caused. For this purpose, the control means can control the actuating device in the first phase with a first signal of low edge steepness, whereas this control means controls the actuating device in the second phase with a second signal of high edge steepness. A fluid movement in the first and second fluid lines is therefore substantially inertia independent in the first phase, whereas a fluid movement in the second phase is essentially determined by the relation of the fluid inertias in the first and second fluid lines.

Alternatively, the displacer, when implemented as a membrane, can be adapted to be pretensioned by the actuating device such that it occupies a first position, the membrane being not fixedly connected to the actuating device so that, in response to an actuation of the actuating device at the beginning of the first phase, the movement of the membrane from the first position to the second position will take place only due to the restoring force of the membrane. This is another possibility of causing a small volume change of the pressure chamber volume per unit time when the displacer moves from the first position to the second position. The restoring force of the membrane is preferably dimensioned such that the negative pressure caused by the restoring force in the pressure chamber is smaller than a capillary pressure prevailing in the second fluid line.

The present invention additionally provides a method of calibrating a microdosing device of the above-mentioned type so that, after a single calibration, reproducible results are obtained during subsequent dosing phases. The microdosing device according to the present invention can also be used as a pipette by immersing, during the above-mentioned first phase, the outlet opening into a fluid to be pipetted.

When the microdosing device is put into operation for the first time, the pressure chamber and the fluid lines are first filled with a fluid prior to activating the actuating device in the first phase for sucking in a fluid. The microdosing device according to the present invention can be produced in an advantageous manner making use of micromechanical methods, especially methods in the field of semiconductor technology. Furthermore, the microdosing device according to the present invention can have a modular structural design of such a nature that e.g. the pressure chamber, the displacer and, optionally, at least parts of the first and of the second fluid line are implemented as a replaceable module by means of micromechanical methods. Furthermore, the media reservoir can be a part of the replaceable module; in this case, it is also produced by means of micromechanical methods.

As has already been explained, an essential advantage of a dosing process according to the present invention is to be seen in the fact that a fluid jet as a whole is discharged and that there is no need of adding a plurality of individual drops for obtaining the desired dosing volumes e.g. in the field of biotechnology. Although the exact tearing of the free jet at the outlet opening is influenced by the properties of the media, as in the case of conventional systems, a higher dosing accuracy is still obtained according to the present invention. Since the media displacer of the microdosing device according to the present invention is easily able to discharge also larger volumes in the desired range between 0.01 µl and 0.1 µl in the course of a process, volume errors, which are a result of the tearing of the individual drops and which would represent a comparatively large relative error in the case of drop volumes of 0.0001 µl, are no longer of any importance. A summation of the systematic errors per drop no longer occurs according to the present invention.

When the displacer is being returned to the second position, whereby the volume of the pressure chamber is reduced, so as to eject the fluid through the outlet opening in the form of a free jet, the movement of the fluid in the first fluid line, i.e. the reservoir channel, and in the second fluid line, i.e. the nozzle channel, is determined almost exclusively by the relation between the fluid inertias in the respective fluid lines, the relation between the flow resistances of the fluid lines being, however, negligible. The defined fluid volume, which is ejected by means of the microdosing device according to the present invention, is therefore almost independent of the viscosity, surface tensions, etc. of the medium to be dosed. The present invention can therefore be used for dosing media having different viscosities and surface tensions, this kind of media being used e.g. in the field of biotechnology.

The microdosing device according to the present invention can also be used for pipetting a fluid and a liquid, respectively. For this purpose, a fluid is sucked in via the outlet opening, which can also be referred to as nozzle, e.g. by immersing the nozzle into a fluid to be pipetted. Subsequently, the sucked-in fluid is discharged in a free jet, as has already been described. Sucking in can be effected e.g. by a negative pressure in the media reservoir, which causes a suction effect, or by a suitable movement of the actuator. The microdosing device according to the present invention is also suitable to be used as a pipette in the case of which the outlet opening of the pressure chamber filled with an inert fluid is immersed into a fluid to be pipetted during the first phase, or a previously unfilled system is filled due to a capillary action alone, when the system is being immersed into the fluid.

Further developments of the present invention are disclosed in the dependent claims.

BRIEF DESCRIPTION OF THE DRAWINGS

In the following, preferred embodiments of the present invention are explained in detail making reference to the drawings enclosed, in which.

DESCRIPTION OF PREFERRED EMBODIMENTS OF THE INVENTION

Figure 1:
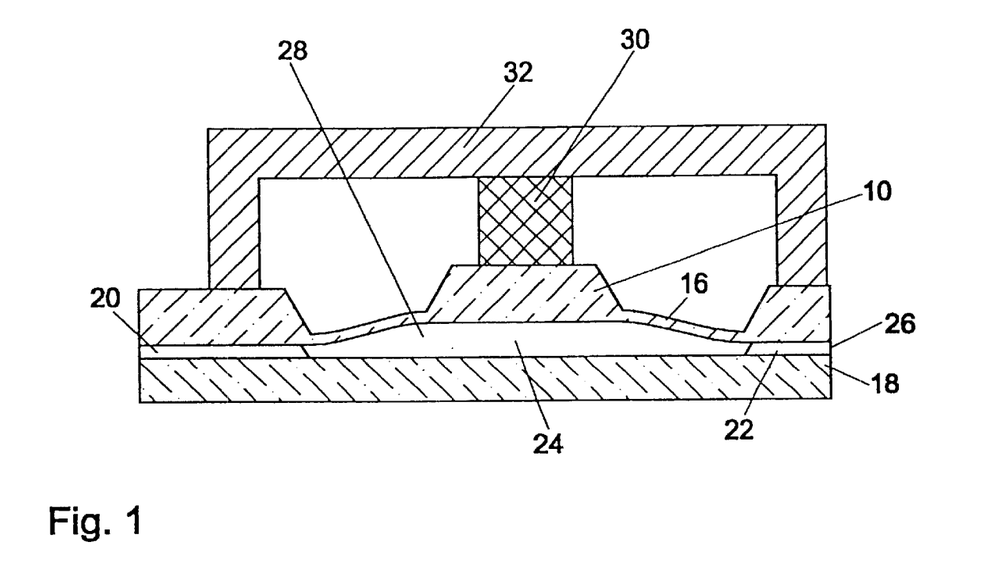
FIG. 1 shows a schematic cross-sectional representation for illustrating the operation of an embodiment of the microdosing device according to the present invention.

FIG. 1 shows a possible embodiment of the microdosing device according to the present invention, which is particularly suitable for producing the dosing element by means of semiconductor-technological methods. In the embodiment shown, the media displacer 10 is realized as a stiffened membrane which is etched in silicon. The displacer structure is produced by means of anisotropic KOH etching which results in the trapezoidal recesses defining the membrane 16. In addition to a stiffened membrane, it is also possible to use a non-stiffened membrane.

In the embodiment of the present invention shown in FIG. 1, the displacer structure 10 is connected to a Pyrex glass plate 18 by means of anodic bonding. In the preferred embodiment, recesses are provided in the silicon wafer in which the displacer structure 10 is defined, the recesses defining a reservoir channel 20, a nozzle channel 22 and a pressure chamber 24. The nozzle channel 22 is in fluid communication with an outlet opening 26, which is indicated by broken lines in FIG. 1. The outlet opening 26 can be implemented in the form of a nozzle. The reservoir channel 20 is in fluid communication with a media reservoir (not shown). The pressure chamber 24 defines a dosing volume 28 which is adapted to be controlled by a movement of the displacer. In the embodiment shown in FIG. 1, a piezo-electric actuating device, which is a piezo-stack actuator 30 in the embodiment shown, is attached via an abutment 32 to the central stiffened area of the displacer in such a way that the media displacer 10 can be moved by actuating the piezo stack 30. The piezo stack 30 is electrically connected to a control means (not shown).

The pressure or dosing chamber 24, the fluid lines 20, 22 and the outlet opening 26 can be produced in the silicon wafer e.g. by standard etching techniques. The dosing chamber and the fluid lines can be sealed hermetically by connecting the silicon wafer to a Pyrex plate (glass) by means of anodic bonding. Apart from the piezo-stack actuator shown, a piezo bending transducer or a piezo plate could be used as alternative drive means. It is, however, apparent that the present invention is not limited to piezoelectric drive means, but that also other drive means, e.g. electro-magnetic or electrostatic ones, can be used.

The reservoir channel, the pressure chamber, the nozzle channel and the displacer membrane are preferably produced by anisotropic KOH etching leading to trapezoidal or triangular channel cross-sections. Other arbitrary cross-sectional shapes can, however, be used as well, e.g. trenches with vertical walls produced by dry-etching techniques.

In addition to the above-described structural design, the channels and the recesses of the micromechanically produced microdosing device according to the present invention can also be structured in Pyrex glass instead of being structured in silicon; it is also possible to use a combination of structuring in silicon and Pyrex glass for realizing the channels and recesses. The magnitude of the determinative parameters, flow resistance, fluidic inductance and capillary pressure, is determined by the length and the etched depth of the channels. The etched depths of the two channels and of the pressure chamber can be varied independently of one another by a multimask process.

As can be seen in FIG. 1, a membrane 16 with a central stiffened area is preferably used as a media displacer 10. The central stiffened area can then preferably be used as a surface for attaching the actuator 30. When a stiffened membrane is used as a media displacer 10, the dosing range can be adapted via the membrane width in the case of a given displacement path of the actuator.

Making reference to FIG. 2, a dosing process according to a preferred embodiment of the present invention will be explained in detail in the following.

First of all, the arrangement, i.e. the fluid lines 20 and 22 and the pressure chamber 24, are filled for the first time either independently by capillary forces or by means of external support by applying pressure to the media reservoir, pumping in the medium or sucking in the fluid, e.g. by producing a negative pressure at the outlet opening. At the location of outlet opening, or nozzle, a discharge of the medium is prevented by the surface tension, whereas a return flow of the medium towards the dosing chamber is prevented by capillary forces, i.e. the meniscus of the fluid will automatically adjust itself to the position of the nozzle. After the first filling, which is only necessary e.g. when a first dosing process is carried out after a prolonged non-operative phase of the dosing device according to the present invention, the steps described hereinbelow will be executed.

Figure 2:
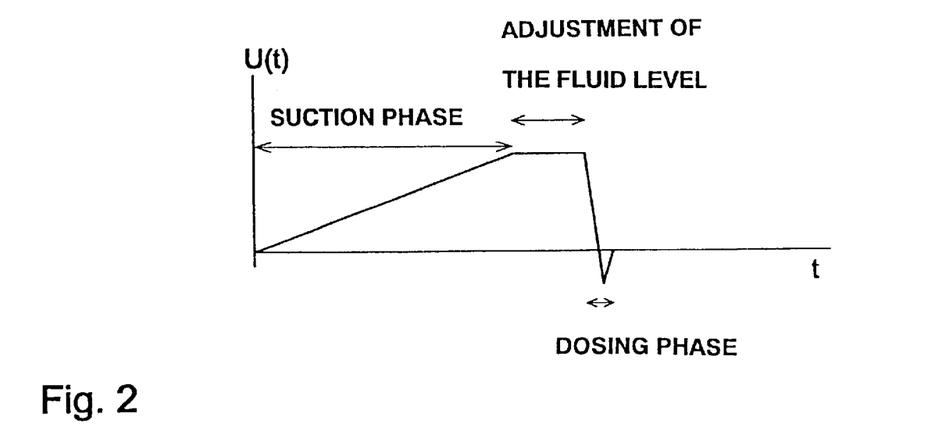
FIG. 2 shows a diagram which shows a control signal for controlling the actuating device of the microdosing device according to the present invention.

During an interval referred to as suction phase in FIG. 2, a control signal, U(t), with low edge steepness is first applied to the actuating device. This causes the membrane to move slowly from its starting position, whereby fluid to be dosed is sucked from both channels, i.e. nozzle side and reservoir side, into the dosing chamber. The low edge steepness of the control signal has the effect that little acceleration is imparted to the fluid to be dosed. Depending on the flow resistance and the capillary pressure of the individual channels, the membrane sucks different subvolumes out of the two channels. Due to the slow process, the inertia of the fluid can be neglected. In this process it should, however, be taken care that the nozzle channel is not emptied completely, since air would then penetrate into the dosing chamber. This can be guaranteed by adapting the control of the actuator, i.e. the edge steepness of the control signal, to the relation between the flow resistances of the fluid line connected to the media reservoir and of the fluid line connected to the nozzle.

Subsequently, a phase which is referred to as "adjustment of the fluid level" takes place in the case of the embodiment of the method according to the present invention shown in FIG. 2. This adjustment of the fluid meniscus to the nozzle end takes place automatically due to capillary forces and surface tensions. The duration of this process is determined by the flow resistance of the channels and perhaps by that of the dosing chamber—the flow resistance of the dosing chamber being, however, negligible in most cases in comparison with the flow resistance of the channels—the physical properties of the medium, i.e. the viscosity, and the hydrostatic pressure prevailing in the reservoir. This adjustment phase of the fluid level is optional, since it can be dispensed with, provided that the suction phase takes place in a sufficiently slow manner, the fluid meniscus being then always at the location of the nozzle.

In a third phase, referred to as "dosing phase" in FIG. 2, the displacer is returned very rapidly to its starting position by a suitable control of the actuating device with the aid of the control means. This is realized by a control signal having a large edge steepness and imparting a high acceleration to the fluid. This has the effect that fluid is ejected through the nozzle as a free jet. Under these circumstances, the movement of the fluid in the reservoir channel and in the nozzle channel is determined almost exclusively by the relation between the fluid inertias in the respective fluid lines, whereas the relation between the flow resistances is negligible. If the inertia of the fluid in the fluid line between the dosing chamber and the nozzle is small in comparison with the inertia of the fluid in the fluid line between the dosing chamber and the reservoir, the flow of fluid back into the reservoir is negligible. If the inertia of the fluid in the reservoir channel is, however, not negligible, the return flow resulting therefrom can be determined by a calibration and compensated for during a subsequent dosing process. This is possible because the inductance L, i.e. the inertia, of a fluid line depends only on the geometry data thereof, L=length of the line/cross-section of the line, but not on the physical properties of the fluid contained in the fluid line.

The ratio of the accelerated amounts of fluid in the direction of the nozzle and in the direction of the reservoir when the displacer changes rapidly, i.e. when flow resistances are neglected, is given by:

$$\frac{d\Phi_d}{d\Phi_r} = \frac{\frac{d\Phi_d}{dt}}{\frac{d\Phi_r}{dt}} = \frac{\frac{\Delta p_d}{\rho L_d}}{\frac{\Delta p_r}{\rho L_r}} = \frac{\Delta p_d L_r}{\Delta p_r L_d} \approx \frac{L_r}{L_d} \quad (eq.\ 1)$$

wherein $\Phi_d$ and $L_d$ stand for the volume flow and the inductance in the direction of the nozzle, and $\Phi_r$ and $L_r$ stand for the volume flow and the inductance in the direction of the reservoir.

Normally the hydrostatic pressures, which can result from the differences in height between the filling level in the reservoir and the position of the nozzle, and the pressure differences between the ambient air pressure and the pressure in the reservoir chamber are both negligible in comparison with the pressures which are applied to the pessure chamber when the displacer changes rapidly and which can amount to several bar. Hence, the pressure differences $\Delta p_d$ and $\Delta p_r$ are almost identical, and, consequently, a fixed relation exists between the fluid flow amounts in the direction of the nozzle and in the return direction. This relation is independent of the viscosity and the density $\rho$ of the fluid contained. The volume lost due to the return flow through the reservoir channel in the first phase of the dosing process, i.e. the slow movement of the displacer for increasing the pressure chamber volume, can therefore simply be taken into account.

Figure 3A:
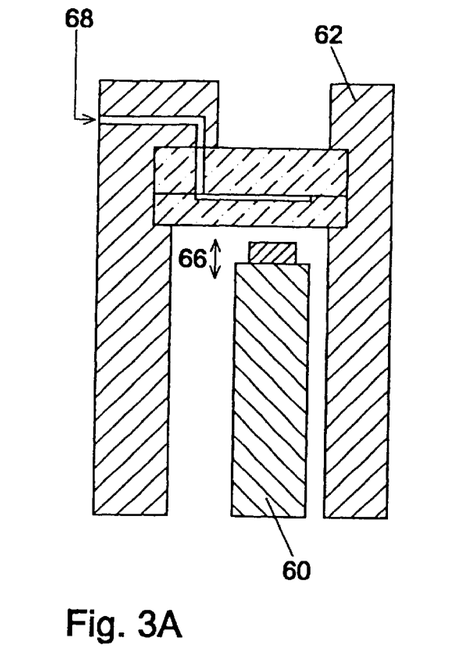
FIGS. 3A, 3B and 3C show schematic representations of embodiments for realizing the microdosing device according to the present invention.
Figure 3B:
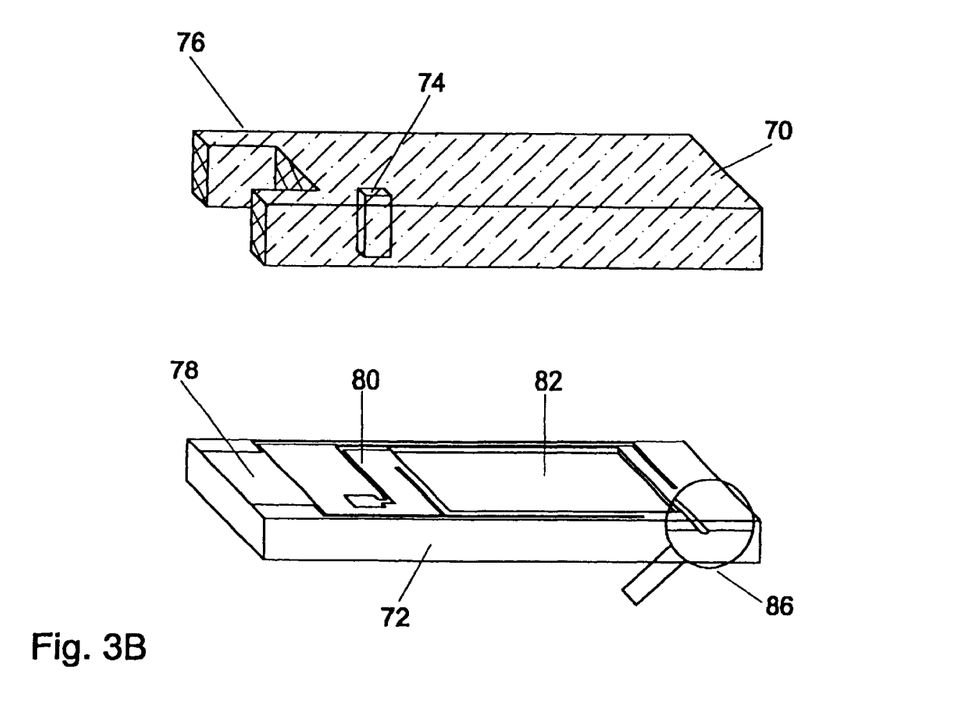
Figure 3C:
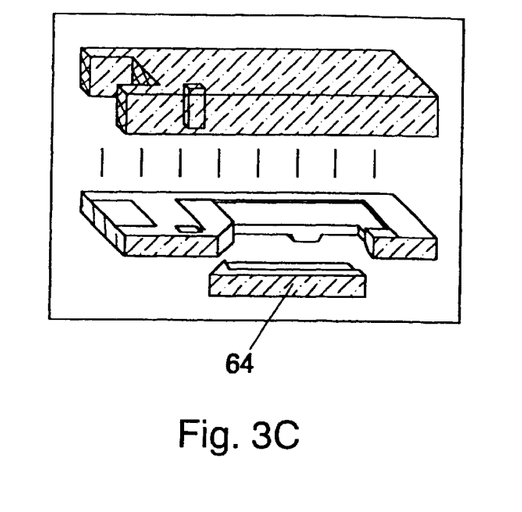

The movement of the displacer during ejection of the fluid can be carried out directly to the position of rest. Alternatively, the movement of the displacer during ejection of the fluid can be finished with a small countermovement, as can again be seen in FIG. 3, cf. the end of the dosing phase. This countermovement causes a counteracceleration which can support the tearing of the jet of fluid.

The movement of the displacer in the suction phase, which produces a defined change of volume per unit time corresponding to a suction volume flow, causes a negative pressure in the pressure chamber; in the dosing process, i.e. when the device according to the present invention is used as a dispenser, this negative pressure must not exceed specific values depending on the suction volume flow and the viscosity. In the case of a small suction volume flow and a low viscosity, the negative pressure is smaller than the capillary pressure in the second fluid line between the pressure chamber and the nozzle so that the second fluid line will remain completely filled with fluid during the whole period of time and so that suction will be effected exclusively from the media reservoir. The risk of air being sucked in through the nozzle channel can be excluded in this way.

In the case of a large suction volume flow and a high viscosity, the negative pressure will, however, exceed the capillary pressure of the second fluid line. Hence, the fluid volume will be sucked in through both fluid lines. If air does not penetrate into the dosing chamber in the course of this process, the line system will refill completely, as has been explained hereinbefore, up to the outlet opening due to capillary forces when the displacer movement has been finished. In this case, the fluid level adjustment phase taking place between the suction phase and the dosing phase is provided.

Further alternative embodiments of the microdosing device according to the present invention will be explained in the following. In the initial state of the dosing cycle, the displacer can be pretensioned and held by the actuator at this position, e.g. forced into the dosing chamber. The displacer can in then be moved in the direction of a further pretension by a further displacement of the actuator. When the actuator displacement decreases, the displacer will move in a direction opposite to the direction of pretension due to its restoring force alone. Making use of this variant, a fixed connection between the actuator and the displacer can be dispensed with. A possible adhesive connection between the actuator and the displacer is not necessary and the assembly work required is essentially reduced.

The above-described alternative of using the actuator and the displacer without any fixed connection permits a modular structural design of the dosing element. Such a structural design is shown in FIGS. 3A and 3B for the purpose of illustration. The electronics and the drive, e.g. a piezo-stack actuator 60, are fixedly installed in a housing 62, whereas a chip 64 including the media displacer is replaceable. The arrow 66 in FIG. 3A indicates the direction of movement of the piezo-stack actuator. Furthermore, a fluid line 68, which extends through the housing, is shown in FIG. 3A. The part of FIG. 3A on the right-hand side shows an enlargement of the micromechanically produced components of the microdosing device, the Pyrex plate and the silicon chip being shown separately.

An enlargement of these micromechanically produced components of the microdosing device is shown in FIG. 3B, in a drawn-apart form. These components are defined by a Pyrex plate 70 which is connected to a silicon chip 72, e.g. by means of anodic bonding. A fluid line 74, which is in fluid communication with a media reservoir (not shown), extends through the Pyrex glass plate 70. The Pyrex glass plate 70 is additionally provided with a recess 76 so as to permit electric contacting of terminal areas 78 on the silicon chip. The reservoir channel is shown designated by reference numeral 80, whereas the dosing chamber is shown designated by reference numeral 82. By means of a further enlargement 86, the outlet end or the nozzle of the microdosing device is schematically shown in FIG. 3B.

In the modular configuration described, it will be advantageous when no adhesive connection between the actuator and the displacer is required, but only a mechanical contact for producing a pretension, as has been described hereinbefore.

Furthermore, it will be advantageous to coat the nozzle with a hydrophobic material, since this will increase the surface tension and suppress a flow of fluid out of the nozzle in the inoperative state still further. In this respect, it will be particularly advantageous to provide a coating of hydrophobic material outside of the nozzle in the neighbourhood along the circumference of the nozzle. Also the inner surface of the second fluid channel may, however, be provided with a hydrophobic coating.

The outlet opening of the devices according to the present invention can, alternatively, be implemented as a nozzle array having e.g. 10 nozzles. An array of jets of fluid can be produced in this way, each individual jet containing only one tenth of the total dosing volume. The functionality of so-called multi-channel pipettes is obtained in this way, these multi-channel pipettes being used for dosing into so-called microtitration plates. Furthermore, in comparison with the use of one large nozzle, the capillary force acting on the discharge side will be stronger when a plurality of small nozzles is used, whereby a return flow will be reduced in cases in which a signal of low edge steepness is used as a control signal.

In alternative embodiments of the present invention, it is also possible to implement a vertical arrangement of the nozzle relative to the chip, in addition to the described planar arrangement of nozzle and chip, the fluid being then discharged from the nozzle at right angles to the chip. A vertical arrangement is adavantageous insofar as the dosing device, i.e. the actuator, the chip and the nozzle, can have an axial structural design; this corresponds to the habit of the users of e.g. conventional pipettes.

A suitable adaptation of the microdosing device according to the present invention to a desired dosing volume V with a maximum permitted dosing inaccuracy dV is preferably carried out in the manner described hereinbelow.

The inaccuracy dV of the total dosed volume corresponds approximately to the size of an individual drop which hypothetically tears at the nozzle and the diameter of which results, in turn, from twice the nozzle diameter in a first approximation. Assuming a spherical drop ($dV=\frac{1}{3}d^3\pi$), the following estimation is obtained for the upper limit of the nozzle diameter d:

$$d < (3dV/4\pi)^{1/3}$$

When the desired dosing accuracy is 1 nl, this means that a nozzle diameter of <60 μm has to be chosen.

Furthermore, the present invention uses an actuator having sufficient power to displace the desired volume V through the nozzle by means of a deflection of a flexible wall of the dosing chamber within a very short period of time; this period of time must be so short that the drops actually tear at the nozzle due to their acceleration. For calibrating the microdosing device according to the present invention, the ratio of the fluid amount displaced in the direction of the nozzle and of the fluid amount displaced in the direction of the reservoir can be determined once, so to speak on the part of the manufacturer. During subsequent dosing processes, the loss of fluid in the direction of the reservoir can then be compensated by a correspondingly larger displacement effected by the displacer.

The microdosing device according to the present invention can also be used as a pipette. In so doing, the nozzle or the outlet opening is immersed into the medium to be pipetted for taking up fluid. The boundary layer between the fluid in the nozzle channel and the ambient air is replaced by a boundary layer between two fluids. The fluid in the dosing chamber is to be regarded as an inert piston which only represents an incompressible medium that does not interact with the fluid to be pipetted. Since the boundary surface to air no longer exists, the capillary pressure in the second fluid line, i.e. between the pressure chamber and the outlet opening, is substantially reduced, since it is compensated partly or fully or perhaps even overcompensated by the capillary pressure of the incoming fluid. In the following, the sequence of pipetting steps will be explained.

The nozzle is held into the fluid to be taken up, whereupon the displacer is moved from the first to the second position. This movement corresponds to the suction phase shown in FIG. 2. The process is now essentially determined by the partial pressure in the dosing chamber and the flow resistance in the fluid line. The flow channels of the nozzle should be implemented such that mixing of the two fluids is suppressed as far as possible. The movement of the displacer during this suction process is compensated not only by a fluid flow of the medium to be pipetted through the nozzle, but partly also by a volume flow from the reservoir into the dosing chamber. Hence, the change of volume effected by the displacer must be larger than the volume to be pipetted that has to be taken up. This problem can be solved in two ways.

On the one hand, the displacer can be controlled such that it executes a markedly larger volume movement so that the amount compensated by taking up the medium to be pipetted will in any case be larger than the desired amount discharged subsequently. Alternatively, the nozzle can be removed from the medium to be pipetted, whereupon the displacer will be returned from the second position to the first position by a control signal of low edge steepness. A loss of medium will not occur in the course of this process, provided that the pressure in the dosing chamber is during the whole process lower than the pressure which is necessary for ejecting fluid or for making it flow out. The suction step can now be repeated so that twice the amount of fluid or several times the amount of fluid can be taken up. Subsequently, a dosing phase can take place with the aid of a signal of high edge steepness, as has been described hereinbefore making reference to FIG. 2. When a superflous amount of the medium to be pipetted exists in the nozzle channel, this superfluous amount can be ejected into a waste bin.

Figure 4A:
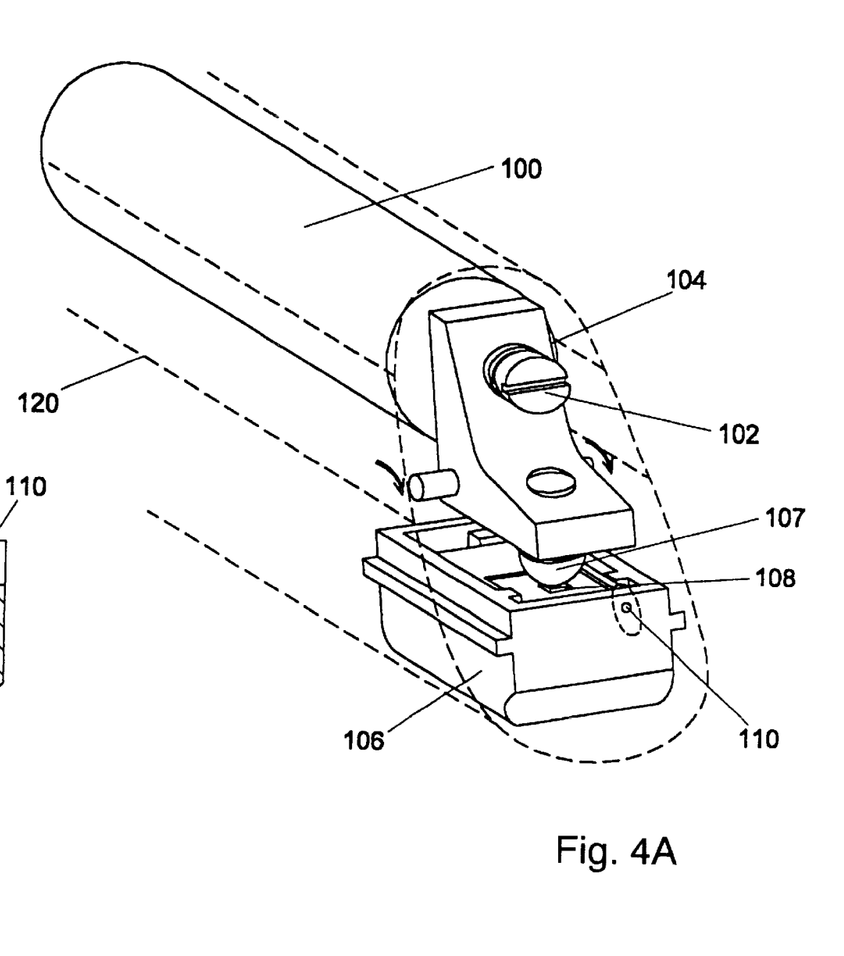
FIGS. 4A & 4B shows a schematic perspective view of a further embodiment of the microdosing device according to the present invention.
Figure 4B:
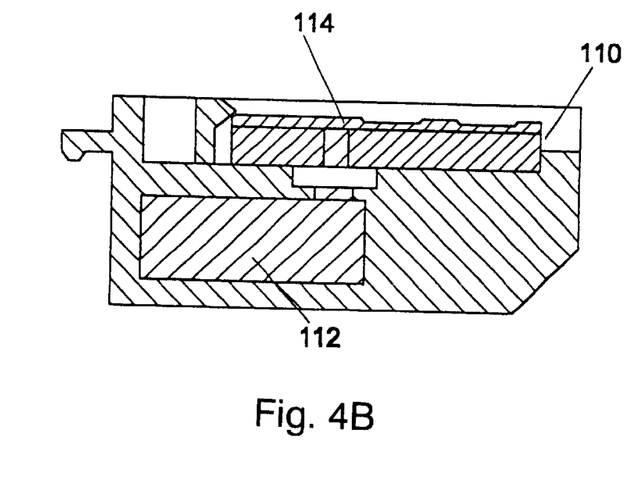

FIG. 4 shows a further advantageous embodiment of a microdosing device according to the present invention. A piezo-stack actuator 100 is connected to a force-transmitting element 104 via a screw connection 102. The force-transmitting element 104 is implemented in the form of a rotatably supported lever-type link which is pivotable in the direction of the arrows shown in FIG. 4. By means of the lever-type link 104 a force produced by the piezo-stack actuator 100 is transmitted to a dosing module 106. The lever-type link 104 is provided with a projection 107 which transmits the force produced by the piezo-stack actuator 100 to a pressure ppoint 108 of the dosing chamber. The nozzle or outlet opening is shown in FIG. 4 designated by reference numeral 110. Alternatively to the lever-type link shown, a hydraulic system could also be used as a force-transmitting element.

The screw connection 102 guarantees together with a spring provided therebelow in this structural design that the lever-type link 104, which is not rigidly connected to the piezoactuator 100 either, is always pressed against the piezoactuator 100.

In the left part of FIG. 4, the dosing module is shown separately, the nozzle 110 being connected to the media reservoir 112 via a fluid line. The dosing chip 114, which comprises at least the pressure chamber and the displacer membrane, is again replaceable in this embodiment. In FIG. 4 a schematic representation of the housing contour of the finished microdosing device is additionally shown by broken lines 120. As can easily be seen from FIG. 4, also the whole fluid module can be replaceable in the embodiment shown.

Also in the embodiment shown in FIG. 4, the actuator and the displacer are not fixedly interconnected. The actuator is only brought into contact with the displacer. This provides a large number of advantages.

On the one hand, it is not necessary to provide any adhesive connection nor any other kind of fastening means so that, as has been explained hereinbefore, the dosing module alone can be exchanged and the actuator can be reused. This is an economy-priced solution when e.g. the dosing module is clogged and when the dosing chip has to be replaced.

Since the contact between the actuator and the displacer only arises through touching, i.e. a fixed connection between these components does not exist, a protective function for avoiding an intake of air through the fluid line between the nozzle and the pressure chamber can additionally be realized. This protective function is achieved as follows. At the beginning of a free-jet dosing process, the actuator is already in contact with the displacer; at this starting position, the displacer is either in force-free contact with the actuator or it may also be predeflected to a certain extent. When the displacer is moved in the second phase, for ejecting a fluid from the nozzle, the actuator will therefore push the displacer in front of it. The increasing degree of deflection of the displacer causes an increase in the restoring force acting on the actuator, the contact between the actuator and the displacer being maintained during the whole movement due to this restoring force.

When the displacer is moved back during the suction phase, the actuator cannot apply any tension forces to the displacer, since a fixed connection does not exist between the actuator and the displacer. Only two cases are imaginable, depending on whether the movement of the actuator or the movement of the displacer is the slower one. When the actuator is moved back at a sufficiently low speed, the temporal movement of the actuator will simultaneously limit the temporal movement of the displacer and therefore also the suction volume flow. The actuator and the displacer remain constantly in contact, since the restoring force of the displacer causes a movement in the same direction.

When the actuator is, however, moved back at a high speed, the contact with the displacer will get lost during this process. In this case, the restoring force of the displacer is not strong enough for following the actuator. The cause is that a negative pressure is generated in the dosing chamber by the restoring force of the displacer. Depending on the vicosity of the medium and the geometry of the channels, this negative pressure leads to a defined suction volume flow through the first and second fluid lines, as has been explained hereinbefore. The contribution of one fluid line to the total volume flow is essentially established according to the effective flow resistances of both fluid lines and the capillary pressure which is additionally effective in the second fluid line. If this suction volume flow is smaller than the volume flow that would correspond to the actuator movement, it will prevent a correspondingly fast relaxation of the displacer and cause the displacer to return to the starting position more slowly than the actuator.

The above-mentioned effect can now be utilized for limiting the maximum negative pressure prevailing in the dosing chamber and, consequently, the maximum suction volume flow. If, e.g. by means of a sufficiently thin membrane, the restoring force of the displacer is dimensioned so small that the maximum negative pressure that can be achieved by the displacer in the dosing chamber is smaller than the capillary pressure in the second fluid line, this fluid line will remain filled with fluid during the whole period of time and suction will be effected exclusively from the media reservoir. Hence, air cannot be sucked in through the second fluid line. In addition, small volume changes of the pressure chamber volume per unit time are constantly caused by this effect during the suction phase.

As has been explained hereinbefore, the non-existing fixed connection between the displacer and the actuator can therefore be regarded as an incorporated protective device for preventing an intake of air.

In the embodiments shown in FIGS. 3A, 3B and 4, a fine adjustment of the actuator in the range of a few $\mu$m must be carried out when the dosing module has been inserted. A micrometer screw is provided for this mechanical fine adjsutment of the actuator. This micrometer screw is not shown in the figures because it is preferably located on the side facing away from the piezo-stack actuator in the housing. A fine adjustment can, however, also be carried out automatically by detecting the contact between the displacer and the actuator by a sensor, e.g. a capacitive distance sensor, an electric circuit, etc. For an automatic fine adjustment making use of a closed circuit as a contact sensor a very low voltage, e.g. in the order of 1 V, is applied between the actuator, i.e. the force-transmitting element in the embodiment according to FIG. 4, and the dosing module. When the actuator or force-transmitting element and the displacer mechanically contact each other, a circuit will be closed, whereupon a corresponding electrical signal will exist. The positioning can also be carried out automatically by changing the voltage applied to the actuator until the closed circuit indicates that there is a contact between the actuator or force-transmitting element and the displacer. The voltage ascertained in this way can then be superimposed onto all other signals as an offset. Hence, it is possible to carry out a fully automatic fine adjustment.

The operation of the microdosing device according to the present invention is, at least in a sufficiently large operating range, independent of the viscosity of the medium to be dosed, provided that the drive is implemented such that it is sufficiently strong, e.g. by means of a piezo-stack actuator, and provided that the displacer membrane is sufficiently stiff, e.g. a silicon membrane with a central stiffened area. Alternatively to a piezo-stack actuator, it is also possible to use mechanical springs as well as electrostatic or hydraulic actuating elements as drive members. Roughly speaking, the dosing error can thus be reduced by the number of individual drops comprised in the fluid amount by means of the microdosing devices according to the present invention. The operation of the microdosing devices according to the present invention can be improved still further by taking care that most of the fluid is ejected through the nozzle, whereas only a small amount flows back in the direction of the reservoir. However, even if such a preferential direction does not exist, the ratio of the respective flow amounts is constant, independently of the viscosity and the temperature, and can therefore be corrected.

According to a further preferred embodiment of the present invention a forcibly controlled displacer, i.e. an actuator without feedback and a displacer which is as stiff as possible, are used for improving the dynamics and for providing thus the possibilities of accelerating also highly viscous media to a sufficient extent.

Figure 5:
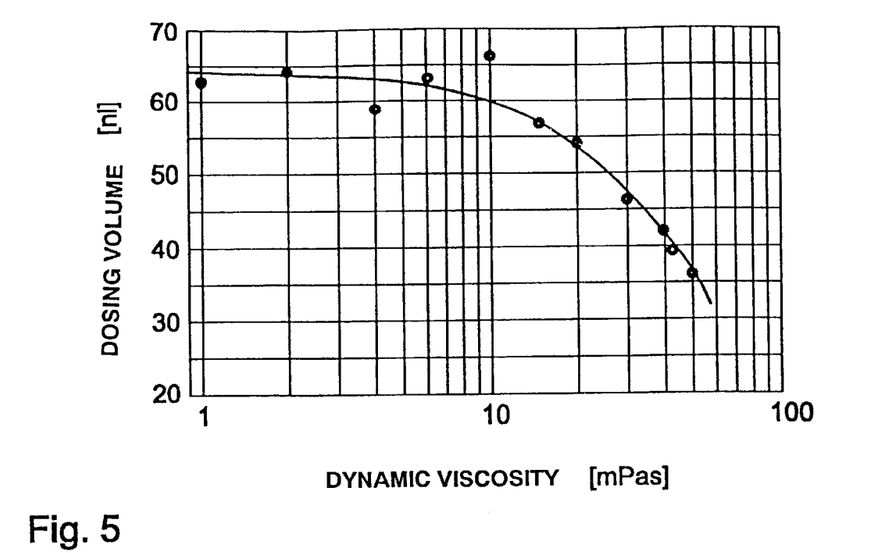
FIG. 5 shows a representation of the dosing volume plotted against the dynamic viscosity.

In FIG. 5, the dosing volume in nl is plotted against the dynamic viscosity in mPas. As can clearly be seen from the characteristic shown in FIG. 5, a recognizable dependence of the dosing volume on the viscosity only occurs from a viscosity range of approx. 20 mPas onwards. For determining the characteristic shown in FIG. 5, glycerin-water solutions in different mixing ratios were used as media.

Figure 6:
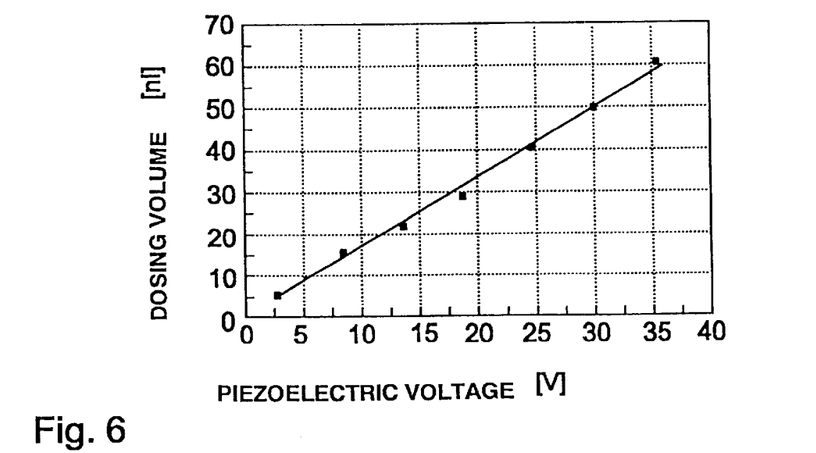
FIG. 6 shows a representation of the dosing volume plotted against the piezoelectric voltage.

FIG. 6 shows the dependence of the dosing volume on the piezoelectric voltage applied to the actuating device. As can be seen in FIG. 6, a substantially linear characteristic is obtained; the medium used as a test medium was water.

The microdosing devices according to the present invention are additionally suitable for constructing a microdosing device array. In such an array a plurality of microdosing devices according to the present invention can be arranged in an arbitrary juxtaposed relationship, i.e. parallel to one another, and controlled individually. It is then possible to arrange e.g. four nozzles within an area of less than one square millimetre and to address these nozzles individually. By means of such a microdosing device array different media can be discharged which will mix in the air only after having been ejected. It is also possible to control several dosing devices of the array by one actuating device whose force is distributed via a force-transmitting element to a plurality of dosing devices simultaneously.

Figure 8:
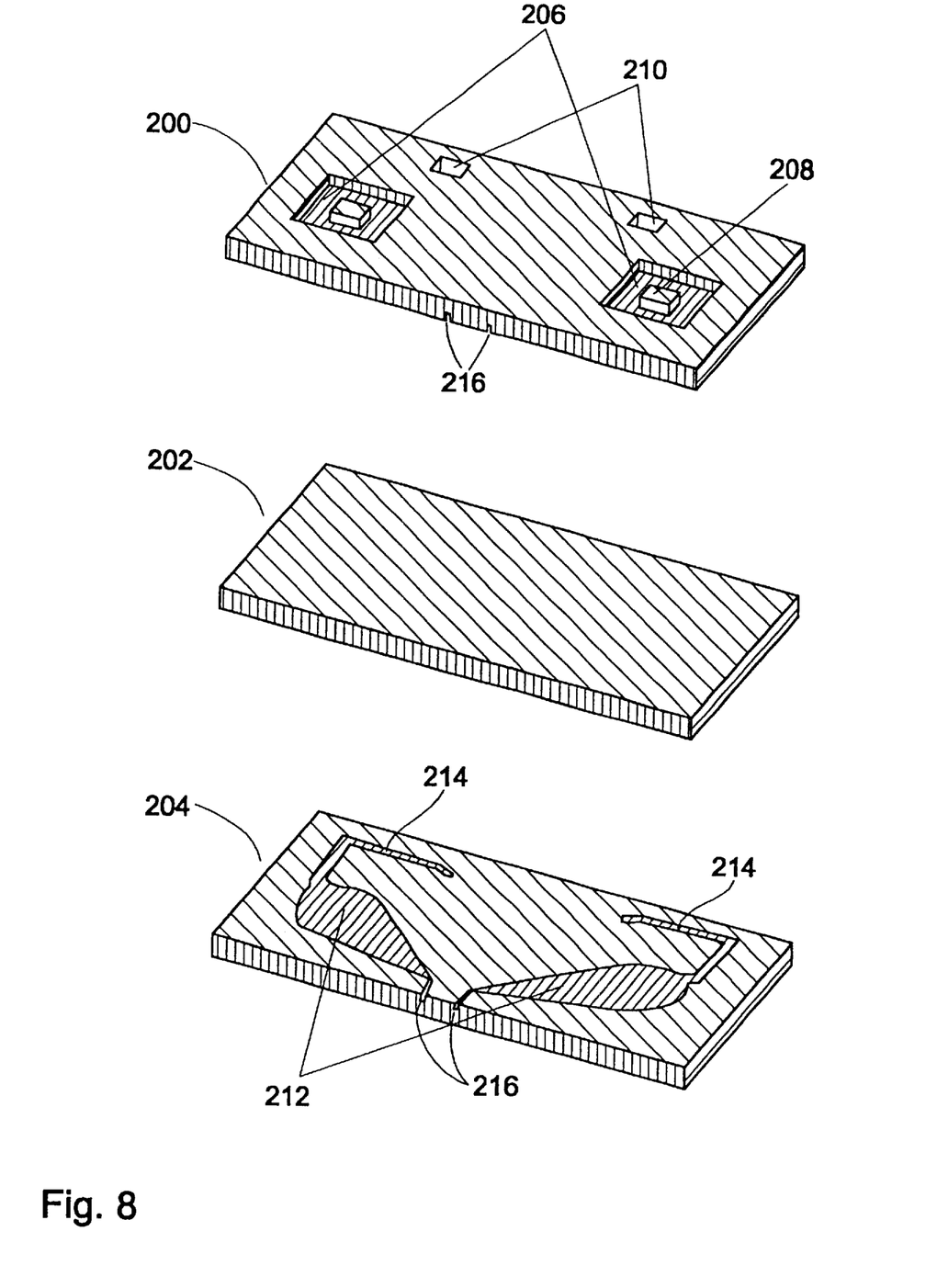
FIG. 8 shows a drawn-apart schematic representation of an array of microdosing devices composed of microdosing devices according to the present invention.
Figure 9:
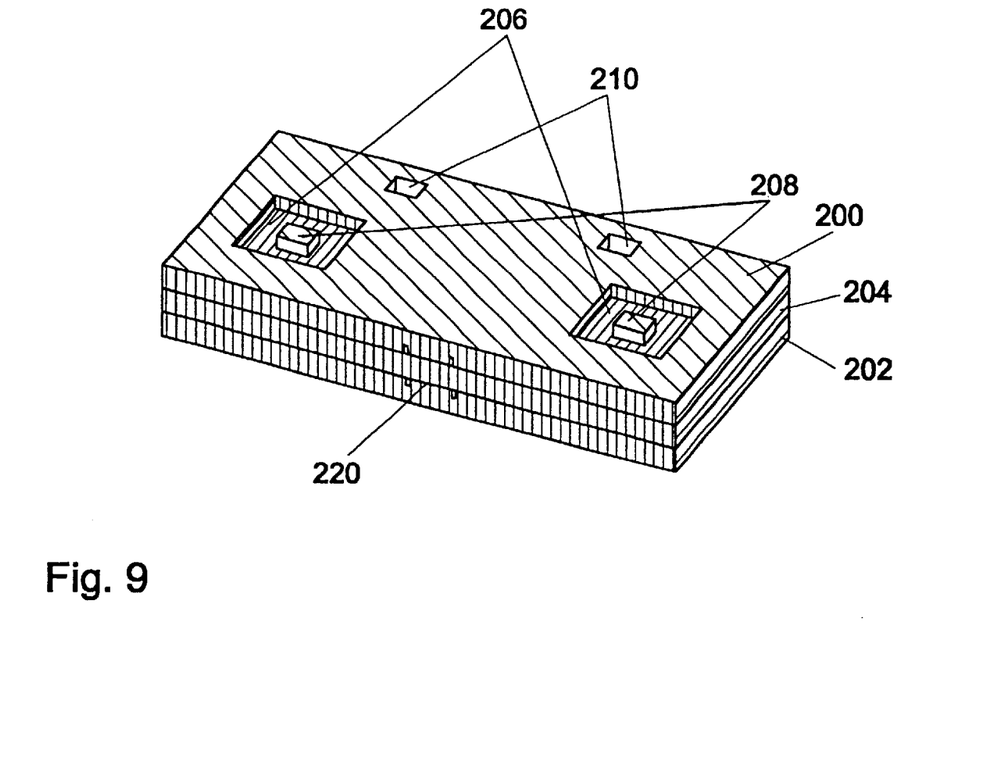
FIG. 9 shows a schematic view of the array of microdosing devices, which is shown in FIG. 8, in the assembled state.

An embodiment of a microdosing device array which is composed of microdosing devices according to the present invention is shown in FIGS. 8 and 9.

As can be seen in FIG. 8, such an array of microdosing devices can be formed of a structure comprising a first silicon layer 200, a Pyrex glass plate 202 and a second silicon layer 204. In the embodiment shown, the structures for two microdosing devices are formed in the first silicon layer 200. Two displacer membranes 206, each provided with a stiffened area 208, are formed in the silicon layer 200 for this purpose. The displacer membranes 206 are adapted to be actuated via the stiffened areas 208. Furthermore, fluid channels 210, which connect the pressure chamber to a media reservoir (not shown), are arranged in the first silicon layer.

The structural design of the second silicon layer 204 is substantially identical with that of the first silicon layer 200. In FIG. 8, the surface of the second silicon layer 204 which is opposed to the surface of the first layer 200 which is shown in this FIG. 8 can be seen. It follows that, with regard to the second silicon layer 204, the pressure chambers 212 formed in this silicon layer 204 and the fluid lines 214 connecting the pressure chambers 212 to a media reservoir can be seen. The fluid lines 214 of a respective silicon layer end in the fluid channels 210 of the respective layer. FIG. 8 also shows the fluid lines which connect the pressure chambers to a respective outlet opening 216.

The Pyrex glass plate 202 is arranged between the two silicon layers 200 and 204 in such a way that the respective main surfaces thereof are connected to the surfaces of the first and of the second silicon layer in which the pressure chambers 212 are formed. It follows that the respective pressure chambers and fluid lines are defined by the structures in the silicon layers and the surfaces of the Pyrex glass plate.

The thus formed structure, which is shown in FIG. 9, is provided with a nozzle array 220 defined by the four outlet openings 216 in the first and in the second silicon wafer. Each nozzle of the 2×2 array 220 has associated therewith a displacer membrane 206 with an associated actuating device (not shown in FIGS. 8 and 9) so that the nozzles can be addressed individually.

It is apparent that, making use of the above-described structural design, microdosing device arrays having an almost arbitrary number of microdosing devices can be constructed. In addition, it is apparent that the fluid channels of the respective pressure chambers can be connected either to the same or to different media reservoirs. Furthermore, microinjection moulding processes and hot-process embossing can advantageously be used for producing the above-described microdosing devices and microdosing device arrays.

In the following, a simplified description of the dynamics of the dosing process will be given. For this purpose, a flow resistance is defined as R and a fluidic inductance as L. The pressure drop across a flow channel is composed of a pressure drop $\Delta p_{laminar}$, which serves to overcome the flow resistance, and a pressure drop $\Delta p_{träge}$ (träge=inert), which accelerates the fluid in the channel. Hence, the following holds true for the pressure difference $\Delta p_{leitung}$ (leitung=line) over the whole fluid line:

$$\Delta p_{leitung} = \Delta p_{laminar} + \Delta p_{träge} \qquad (eq.\ 2)$$

$$\Delta p_{träge} = \rho L \frac{d\Phi}{dt} \qquad mitL = \frac{l}{A}$$

$$\Delta p_{laminar} = \rho R \Phi$$

The flow resistance R and the fluidic inductance L are calculated e.g. for a round hose having the radius r and the line length l as follows:

$$L = \frac{l}{r^2 \pi}; \quad R = \frac{8\eta l}{\rho \pi r^4} \qquad (eq.\ 3)$$

Figure 7:
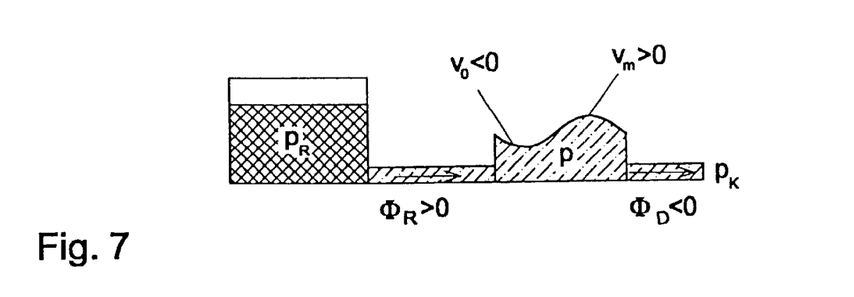
FIG. 7 shows a scheme for describing the dynamics of a microdosing device according to the present invention.

FIG. 7 shows a scheme for describing the dynamics of a microdosing device according to the present invention. $p_R$ represents the pressure in the media reservoir, $p_K$ the capillary pressure and p the pressure in the pressure chamber. $V_m$ corresponds to the volume displaced by the membrane, whereas $V_0$ corresponds to the change of the chamber volume caused by strain on the housing and other perturbing influences. $\Phi_r$ is the volume flow in the reservoir channel and $\Phi_D$ is the flow in the nozzle channel. In the equations following hereinbelow, U corresponds to the control voltage at the actuator.

The following holds true for the fluid line between the dosing chamber and the reservoir:

$$p_R - p = \rho R_R \Phi_R + \rho L_R \frac{d\Phi_R}{dt} \qquad (eq.\ 4)$$

The following holds true for the fluid line between the dosing chamber and the nozzle:

$$p + p_K - p_{Atmosphäre} = \rho R_D \Phi_D + \rho L_D \frac{d\Phi_D}{dt} \qquad (eq.\ 5)$$

The following holds true for the dosing chamber:

$$\frac{dV}{dt} = \Phi_R - \Phi_D$$

$$\frac{d}{dt}(V_m + V_o) = \frac{\partial V_m}{\partial p}\bigg|_U \frac{dp}{dt} + \frac{\partial V_m}{\partial U}\bigg|_p \frac{dU}{dt} + \frac{\partial V_o}{\partial p}\frac{dp}{dt} = \Phi_R - \Phi_D$$

and, consequently, $$\frac{dp}{dt} = \frac{\Phi_R - \Phi_D - \frac{\partial V_m}{\partial U}\bigg|_p \frac{dU}{dt}}{\frac{\partial V_m}{\partial p}\bigg|_U + \frac{\partial V_o}{\partial p}} \qquad (eq.\ 6)$$

It may therefore be stated in summary that the dynamics of the dosing element is by approximation described by three differential equations for the three independent variables $\Phi_r$, $\Phi_D$ and p as follows:

$$\frac{dp}{dt} = \frac{\Phi_R - \Phi_D - \frac{\partial V_m}{\partial U}\bigg|_p \frac{dU}{dt}}{\frac{\partial V_m}{\partial p}\bigg|_U + \frac{\partial V_o}{\partial p}} \quad \text{(eq. 7)}$$

$$\frac{d\Phi_R}{dt} = \frac{p_R - p - \rho R_R \Phi_R}{\rho L_R}$$

$$\frac{d\Phi_D}{dt} = \frac{p + p_K - \rho R_D \Phi_D}{\rho L_D}$$

The following predetermined design parameters are known: $R_R$, $R_D$, $L_R$, $L_D$. Operating parameters are the voltage $U(t)$ and the media reservoir pressure $p_R$. The quantity to be measured is the pressure $p_K$ and the quantities to be measured or to be calculated are $dV_m/dp$, $dV_O/dp$, and $dV_m/dU$.

The differential equation system is to be solved for a predetermined $U(t)$ for the following boundary conditions:
$p(t=0)=0$;
$\Phi_R(t=0)=0$; and
$\Phi_D(t=0)=0$.

What is claimed is:

1. A volume sensor-free microdosing device comprising:
   a pressure chamber which is at least partly delimited by a displacer;
   an actuating device for actuating the displacer, the volume of the pressure chamber being adapted to be changed by actuating the displacer;
   a media reservoir which is in fluid communication with the pressure chamber;
   an outlet opening which is in fluid communication with the pressure chamber; and
   a control means for driving the microdosing device, wherein;
   a first change of volume of the pressure chamber volume is effected per unit time by a movement of the displacer from a first position to a predetermined second position, the second position of the displacer defining a larger volume of the pressure chamber than the first position, thereby causing a fluid volume to be sucked into the pressure chamber; and
   in a second phase, a second volume change of the pressure chamber volume, which is greater than said first volume change, is effected per unit time by a movement of the displacer from a second position to the first position, thereby causing a defined fluid volume to be ejected from the outlet.

2. A volume sensor-free microdosing device according to claim 1, wherein the media reservoir is in fluid communication with the pressure chamber via a first fluid line, and wherein the outlet opening is in fluid communication with the pressure chamber via a second fluid line.

3. The volume sensor-free microdosing device according to claim 1, wherein the control means controls the actuating device in the first phase with a first signal of an edge steepness and in a second phase with a second signal of a further edge steepness wherein said further edge steepness is higher than said edge steepnes.

4. The volume sensor-free microdosing device according to claim 1, wherein the actuating device and the displacer are implemented in a manner which controls the displacer.

5. The volume sensor-free microdosing device according to claim 3, wherein the first signal in the first phase causes a inertia independent fluid movement in the first and second fluid lines, whereas the second signal in the second phase causes an inertia dependent fluid movement in the first and second fluid lines.

6. The volume sensor-free microdosing device according to claim 1, wherein the pressure chamber and displacer are micromechanically produced structures.

7. A volume sensor-free microdosing device according to claim 6, wherein the displacer is realized as a membrane.

8. The volume sensor-free microdosing device according to claim 6, wherein at least parts of the first and second fluid lines, the outlet opening and the pressure chamber are defined by structures in a silicon wafer and/or a pyrex glass plate connected to said silicone wafer.

9. A volume sensor-free microdosing device according to claim 1, wherein the displacer is a membrane, said membrane being adapted to be pretensioned by the actuating device such that it occupies a first position, and the actuating device being not fixedly connected to the membrane in such a way that, in response to an actuation of the actuating device at the beginning of the first phase, the movement of the membrane from the first position to the second position will take place only due to the restoring force of the membrane.

10. A volume sensor-free microdosing device according to claim 1, wherein the actuating device is a piezo-stack actuator.

11. The volume sensor-free microdosing device according to claim 1, wherein an outer surround of the outlet opening is coated in hydrophobic material.

12. A volume sensor-free microdosing device according to claim 1, wherein the outlet opening is formed by an array comprising a plurality of openings.

13. A volume sensor-free microdosing device according to claim 1, which is additionally provided with a means for generating a negative pressure in the media reservoir.

14. A volume sensor-free microdosing device according to claim 1, wherein the control means controls the actuating device between the first and second phases in a third phase for a predetermined period of time in such a way that the displacer remains at the second position.

15. A volume sensor-free microdosing device according to claim 1, wherein the control means controls the actuating device in such a way that the displacer, when moving to the fist position, is initially moved beyond said first position by said actuating device prior to finally reaching said first position.

16. The volume sensor-free microdosing device according to claim 9, wherein the actuating device and the control means are installed in a housing in a fixed position, whereas the pressure chamber, the displacer and/or the media reservoir are adapted to be installed in the housing in a replaceable position.

17. A volume sensor-free microdosing device according to claim 9, wherein the restoring force of the membrane is dimensioned such that the negative pressure caused by said restoring force in the pressure chamber is smaller than a capillary pressure prevailing in the second fluid line.

18. A volume sensor-free microdosing device according to claim 16, which is additionally provided with a fine-adjustment device for positioning the actuating device relative to the displacer.

19. A volume sensor-free microdosing device according to claim 1, wherein a force produced by the actuating device is transmitted to the displacer via a force-transmitting element.

20. A volume sensor-free microdosing device according to claim 19, wherein the force-transmitting element is a rotatably supported lever-type link for converting a force produced by the actuating device into a force acting on the displacer essentially at right angles to said force produced by the actuating device.

21. A dosing device array comprising a plurality of microdosing devices according to claim 1, said microdosing devices being arranged in juxtaposed relationship and being addressable individually.

22. A dosing device array comprising a plurality of microdosing devices according to claim 1, said microdosing devices being arranged in juxtaposed relationship and being controlled by an actuating device whose force is adapted to be distributed via a force-transmitting element to a plurality of microdosing devices simultaneously.

23. A method of calibrating a microdosing device according to claim 1, wherein, prior to the dosing operation, a ratio of a fluid amount displaced in the direction of the media reservoir during the second phase and of a fluid amount displaced in the direction of the outlet opening during said second phase is determined, and wherein during the subsequent dosing processes the fluid amount displaced in the direction of the media reservoir is compensated by a suitably modified control of the actuating device by the control means so as to cause a larger displacement by means of the displacer.

24. The use of a microdosing device according to claim 1 as a pipette, wherein the outlet opening of the pressure chamber filled with an inert fluid is immersed into a fluid to be pipetted during the first phase.

* * * * *